United States Patent [19]

Hartwig

[11] Patent Number: 5,176,150

[45] Date of Patent: Jan. 5, 1993

[54] LAPAROSCOPIC ESOPHAGEAL GASTRIC APPARATUS

[76] Inventor: Ricky G. Hartwig, 3920 81st St., Lincoln, Nebr. 68506

[21] Appl. No.: 880,529

[22] Filed: May 8, 1992

[51] Int. Cl.⁵ .............................................. A61B 7/02
[52] U.S. Cl. .................................... 128/773; 128/715; 128/670; 128/204.23; 128/911
[58] Field of Search ............ 128/773, 670, 715, 207.15, 128/204.23, 911, 202.28, 780, 687; 604/97

[56] References Cited

U.S. PATENT DOCUMENTS

| | | | |
|---|---|---|---|
| 3,951,136 | 4/1976 | Wall | 128/670 |
| 4,176,660 | 12/1979 | Mylrea et al. | 128/715 |
| 4,301,809 | 11/1981 | Pinchak | 128/715 |
| 4,327,720 | 5/1982 | Bronson et al. | 128/911 |
| 4,349,031 | 9/1982 | Perlin | 128/715 |
| 4,484,583 | 11/1984 | Graham | 128/773 |
| 4,497,318 | 2/1985 | Donmichael | 128/202.28 |
| 4,577,638 | 3/1986 | Graham | 128/773 |
| 4,607,643 | 8/1986 | Bell et al. | 128/773 |
| 4,917,107 | 4/1990 | Bell et al. | 128/715 |
| 5,056,514 | 10/1991 | DuPont | 128/207.15 |
| 5,067,497 | 11/1991 | Greear et al. | 128/207.15 |
| 5,076,284 | 12/1991 | Joyce et al. | 128/773 |

Primary Examiner—Stephen C. Pellegrino
Assistant Examiner—Gary Jackson
Attorney, Agent, or Firm—Zarley, McKee, Thomte, Voorhees & Sease

[57] ABSTRACT

An esophageal gastric apparatus includes a first elongated tube with forward and rearward ends, and a second tube inserted within the first tube with the forward end of the second tube projecting from the forward end of the first tube. The rearward end of the second tube projects outwardly through the wall of the first tube adjacent the rearward end of the first tube. The second tube has an outside diameter less than the interior diameter of the first tube, so as to form a cavity between the second tube and the first tube. A plurality of apertures are formed in forward end of the first tube, with a diaphragm surrounding the apertures, so as to transmit sound through the first tube to the rearward end thereof. The second tube has suction ports formed in the forward end thereof to suction fluid and material therethrough.

7 Claims, 1 Drawing Sheet

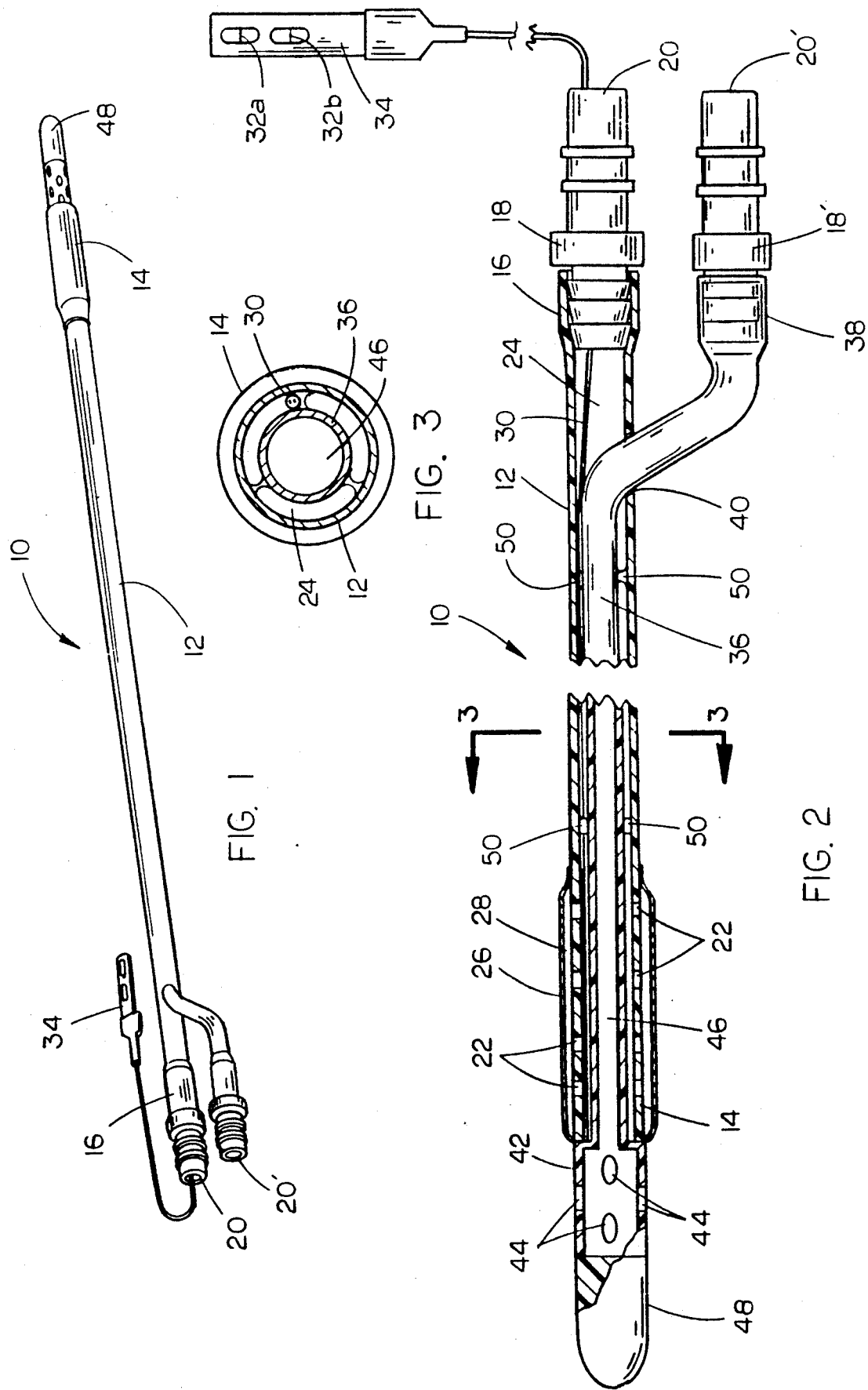

LAPAROSCOPIC ESOPHAGEAL GASTRIC APPARATUS

TECHNICAL FIELD

The present invention relates to apparatus utilized in conjunction with laparoscopies, and more particularly to an improved laparoscopic esophageal gastric apparatus having lumens for gastric suction and for a stethoscope.

BACKGROUND OF THE INVENTION

Anesthesiologists utilize esophageal stethoscopes to monitor heart rhythm and breathing during surgical procedures such as laparoscopies or the like. Such stethoscopes typically include an elongated tube having a separate diaphragm on one end which is inserted within the esophagus. The opposite end of the tube is hooked to an earpiece, and a tube extending from the diaphragm to the upper end of the tube is connected to the anestesiologist's earpiece.

Prior to surgery, it is typical to place an oral gastric or nasal gastric tube in the stomach for suctioning liquids and air. Such suctioning is especially necessary for laparoscopies to prevent gastric performation from the sharp trocars introduced during surgery. These gastric tubes are more difficult to insert within the stomach than an esophageal stethoscope, because the tubes are conventionally smaller in diameter and more flexible. If the initial gastric tube cannot be positioned within the stomach, it is then necessary to utilize a harder tube, which increases the chance of bleeding and potential contamination (infection) to the patient and anesthesia personnel through manipulation.

It is therefore a general object of the present invention to provide an improved esophageal gastric apparatus having dual functions within a single combined apparatus.

These and other objects will be apparent to those skilled in the art.

SUMMARY OF THE INVENTION

The esophageal gastric apparatus of the present invention includes a first elongated tube with forward and rearward ends, and a second tube inserted within the first tube with the forward end of the second tube projecting from the forward end of the first tube. The rearward end of the second tube projects outwardly through the wall of the first tube adjacent the rearward end of the first tube. The second tube has an outside diameter less than the interior diameter of the first tube, so as to form a cavity between the second tube and the first tube. A plurality of apertures are formed in the forward end of the first tube, with a diaphragm surrounding the aperture, so as to transmit sound through the first tube to the rearward end thereof. The second tube has suction ports formed in the forward end thereof to suction fluid and material therethrough.

BRIEF DESCRIPTION OF THE DRAWINGS

FIG. 1 is a perspective view of the present invention;
FIG. 2 is an enlarged partial sectional view through the length of the present invention; and
FIG. 3 is a sectional view taken at lines 3—3 in FIG. 2.

DESCRIPTION OF THE PREFERRED EMBODIMENT

Referring now to the drawings, in which similar or corresponding parts are identified with the same reference numeral, and more particularly to FIG. 1, the esophageal gastric apparatus of the present invention is identified generally at 10, and includes an elongated tube 12 having a forward end 14 and rearward end 16.

Referring now to FIG. 2, rearward end 16 of tube 12 is open, so as to receive a conventional connector 18 with a rearward port 20. Forward end 14 of tube 12 has a plurality of openings 22 therein communicating between the interior cavity 24 of tube 12 and the exterior of tube 12. A thin membrane 26 is sealed to the forward end of tube 12 to form an annular cavity 28 which surrounds openings 22. In this fashion, membrane 26 acts as a diaphragm to transmit sounds through openings 22 to interior cavity 24 of tube 12.

A cord 30 extends from forward end 14 to rearward end 16 of tube 12 within cavity 24, and thence through connector 18 and out port 20. Cord 30 includes a pair of wires 32a and 32b which are separated and exposed on an electrical connector 34 at the rearward end of cord 30. Connector 18 is connected to a conventional anesthesia tube and earpiece worn by an anesthesiologist in a conventional manner. Electrical connector 34 is connected to a temperature box for temperature monitoring. It can therefore be seen that tube 12 acts as an esophageal stethoscope in a conventional fashion.

A second tube 36 is mounted within tube 12 and extends generally coaxially therewith. Tube 36 is an exterior diameter less than the interior diameter of tube 12, so as to form an annular space around tube 36 for the transmission of sound from forward end 14 to rearward end 16 of tube 12. Second tube 36 has a rearward end 38 which projects through an opening 40, to project exteriorly of tube 12. A second connector 18' is mounted in the open end of rearward end 38 and has a port 20' therein communicating with the interior of tube 36.

The forward end 42 of inner tube 36 extends forwardly past the open forward end 14 of tube 12. Forward end 42 is preferably expanded in diameter so as to seal the forward end 14 of tube 12. A plurality of apertures 44 are spaced-apart and staggered around forward end 42 of tube 36, to permit suctioning of material into the lumen 46 of tube 36. Connection of connector 18' with a conventional suction pump will permit the suctioning of fluid and materials from the stomach through apertures 44 and lumen 46.

A soft rubber solid tip 48 is mounted to the extreme forward end of forward end 42, to add firmness to catheter 10 in passing the catheter down the esophagus to the stomach, while reducing the possibility of damage to tissues as apparatus 10 is inserted.

In operation, it can be seen that apparatus 10 provides both gastric suctioning and the benefits of an esophageal stethoscope within a single apparatus. In order to permit the effective functioning of the passage of sound along tube 12, tube 36 is preferably maintained in spaced relationship from tube 12 by a series of support legs 50 spaced radially and longitudinally between tubes 12 and 36, as shown in FIGS. 2 and 3. Legs 50 prevent the inner tube 36 from contacting outer tube 12, which would produce sounds interfering with the operation of esophageal stethoscope of tube 12.

Whereas the invention has been shown and described in connection with the preferred embodiments thereof, it will be understood that many modifications, substitutions and additions may be made which are within the intended broad scope of the appended claims. There has therefore been shown and described a new apparatus which accomplishes all of the above stated objects.

I claim:

1. An esophageal gastric apparatus, comprising:

an elongated first tube having an open forward end, an open rearward end, and a cylindrical wall extending from the forward end to the rearward end;

an elongated second tube having forward and rearward ends, mounted within said first tube with the forward end of the second tube extending forwardly out of the open forward end of the first tube, and the second end of the second tube extending through an opening in the wall of the first tube to project exteriorly of the first tube;

said second tube having an exterior diameter less than the interior diameter of the first tube, forming a cavity between the second tube and the interior of the first tube cylindrical wall;

the forward end of the second tube being mounted to the forward end of the first tube so as to close the forward end of the first tube;

said first tube having means in the forward end thereof for receiving and transmitting sound to the rearward end of said first tube;

said second tube having suction ports formed in the forward end thereof for suctioning fluid and material through said second tube and out through the rearward end thereof.

2. The apparatus of claim 1, wherein the forward end of the second tube is closed, and said suction ports are located on said second tube forwardly of the forward end of the first tube.

3. The apparatus of claim 2, further comprising a soft rubber solid tip mounted on the closed forward end of said second tube.

4. The apparatus of claim 2, wherein said suction ports are spaced-apart and staggered around said second tube so as to resist bending forces in the area of said ports.

5. The apparatus of claim 1, wherein said means for receiving and transmitting sound includes:

a plurality of apertures formed in the forward end of said first tube; and a thin membrane wrapped around the portion of said first tube having said apertures, and spaced therefrom to form an annular cavity between said membrane and said first tube, said membrane sealed to said first tube at a forward and rearward annular edge, so as to act as a sound diaphragm.

6. The apparatus of claim 1, wherein said second tube is mounted coaxial within said first tube to form an annular space therebetween.

7. The apparatus of claim 6, further comprising a plurality of spaced-apart support legs extending between said first and second tubes to prevent direct contact between the walls of the first tube and second tube from the forward end of the first tube to the juncture of the second tube through the wall of the first tube.

* * * * *